US00PP11256P

United States Patent [19]

Segers

[11] Patent Number: Plant 11,256

[45] Date of Patent: Feb. 29, 2000

[54] HYBRID TEA ROSE PLANT NAMED 'PREVERIS'

[75] Inventor: Theodorus A. Segers, Hoofddorp, Netherlands

[73] Assignee: Prego Royalty B.V., Naaldwijk, Netherlands

[21] Appl. No.: 08/929,493

[22] Filed: Sep. 15, 1997

[51] Int. Cl.[7] ..... A01H 5/00

[52] U.S. Cl. ..... Plt./130

[58] Field of Search ..... Plt./11, 130, 134, Plt./135

*Primary Examiner*—Howard J. Locker
*Attorney, Agent, or Firm*—C. A. Whealy

[57] ABSTRACT

A distinct cultivar of hybrid tea rose plant named 'Preveris', characterized by its large yellow and orange flowers; long and strong stems; dark green leaves; and good postproduction longevity.

1 Drawing Sheet

The present invention relates to a new and distinct cultivar of hybrid tea rose plant, botanically known as *Rosa hybrida,* commercially used as a cut flower, and hereinafter referred to by the cultivar name Preveris.

The new cultivar is a product of a planned breeding program conducted by the inventor in Rijsenhout, The Netherlands. The objective of the breeding program was to develop cut rose varieties with novel and attractive flower colors, long and strong stems, dark leaves, and good post-production longevity. The new cultivar originated from a cross made by the inventor in 1993 of two proprietary seedlings. The proprietary selection P151 was the female, or seed, parent, and the proprietary selection 92-331 was the male, or pollen, parent. The cultivar Preveris was discovered and selected by the inventor as a flowering plant within the progeny of the stated cross in a controlled environment in Rijsenhout, The Netherlands.

Asexual propagation of the new cultivar by cuttings taken at Rijsenhout, The Netherlands, has shown that the unique features of this new rose plant are stable and reproduced true to type in successive generations.

The following traits have been repeatedly observed and are determined to be unique characteristics of 'Preveris'. These characteristics in combination distinguish the new rose plant as a new and distinct cultivar:

1. Large yellow and orange flowers.
2. Long and strong stems.
3. Dark green leaves.
4. Good postproduction longevity.

The new rose plant has not been observed under all possible environmental conditions. The phenotype may vary significantly with variations in environment such as temperature, light or fertility level, without, however, any variance in genotype.

BRIEF DESCRIPTION OF PHOTOGRAPH

The accompanying colored photograph illustrates the new rose plant, showing the colors as true as it is reasonably possible to obtain in colored reproductions of this type.

The photograph comprises a top perspective view of typical flowering stems of the new rose plant grown in Rijsenhout, The Netherlands. Flower and foliage color in these photographs may appear different from the actual colors due to light reflectance.

DETAILED BOTANICAL DESCRIPTION

The following observations, measurements, values, and comparisons describe plants grown in Rijsenhout, The Netherlands, under glass with average day temperatures of 19° C. and average night temperatures of 17° C.

In the following description, color references are made to The Royal Horticultural Society Colour Chart except where general terms of ordinary dictionary significance are used.

Classification:

*Botanical.*—*Rosa hybrida* cultivar Preveris.

*Commercial.*—Cut rose.

Parentage:

Male or pollen parent: *Rosa hybrida* proprietary selection 92-331.

Female or seed parent: *Rosa hybrida* proprietary selection P151.

Propagation:

*Type.*—Cuttings.

*Time to initiate roots.*—About 12 days with soil temperatures of 25° C.

*Time to develop roots.*—About 25 days with soil temperatures of 25° C.

*Rooting habit.*—Fine, fibrous and well-branched.

Plant description:

*Form.*—Upright.

*Growth habit.*—Moderately vigorous. Freely branching and dense growth.

*Plant size.*—About 115 cm in height and about 40 cm in width.

*Productivity.*—About 150 stems per square meter per year under greenhouse year-round production.

*Stem and lateral branches.*—Quantity of lateral branches: Typically three. Length of lateral branches: About 100 cm. Internode length: About 7 cm. Color: 147A. Prickles: Present, moderate in number. Length: About 1.1 cm. Color: Apex: 176A. Base: 176A.

*Foliage description.*—Leaves arranged alternately, compound with three, five or seven leaflets per leaf, and generally symmetrical. Of the apical 15 compound leaves, typically the distal two leaves have three leaflets, the next five leaves have five leaflets and the proximal eight leaves have seven leaflets. Quantity of leaves: About 15 per lateral branch. Length, seven-leaflet leaf: About 19 cm. Width, seven-leaflet leaf: About 17 cm. Length of leaflet of five-leaflet leaf: About 8 cm. Width of leaflet of five-leaflet leaf: About 5 cm. Length of leaflet of seven-leaflet leaf: About 9.2 cm. Width of leaflet of seven-leaflet leaf: About 6.4 cm. Shape: Ovate with acute apex and obtuse base. Margin: Serrate. Texture: Leathery, glossy and glabrous. Petiole length: About 4 cm. Petiole diameter: About 3 mm. Stipule: Foliaceous, adnate to petiole. Color: Young foliage, upper side: 200C. Young foliage, under side: 200D. Mature foliage, upper side: 139A. Mature foliage, under side: 147B. Venation, upper side: 139A. Venation, under side: 147B. Petiole: 136A.

Flower description:

*Flower type and habit.*—Large yellow and orange flowers. Consistently symmetrical rosette flowers. Freely and continuous flowering. Flowers borne singly at terminal apices or in clusters of two each. Flowers persistent.

*Flowering season.*—Year-round under greenhouse conditions.

*Rate of flower opening.*—About 9 days.

*Fragrance.*—Faint, pleasant.

*Flower diameter.*—About 11.5 cm.

*Flower depth (height).*—About 6.5 cm.

*Flower longevity on plant.*—About 15 days.

*Flower longevity as a cut flower.*—About 12 days.

*Flower buds.*—Shape: Ovate. Length: About 5.4 cm. Diameter: About 4.1 cm. Color: 11B.

*Petals/petaloids.*—Quantity: About 26 per flower. Typically about four rows with six or seven petals each. Length: About 6 cm. Width: About 6.5 cm. Shape: Rounded with mucronate apex. Aspect: Petals reflex as the flowers open. Margin: Undulate and entire. Texture: Satiny and slightly rippled. Color: Upper side, when opening: Apex, 25B; center and margins, 9A. Under side, when opening: 9A. Upper side, fully opened: Apex, 25B to 38A; center and margins, 9A. Under side, fully opened: 9A. Fading to: 38A.

*Sepals.*—Quantity: Typically five per flower. Calyx length: About 4.4 cm. Calyx width: About 4.6 cm. Shape: Subulate with aristate tip. Color: Upper side: 146D. Under side: 147D.

*Peduncles.*—Strength: Very strong. Aspect: Erect. Length: About 8.5 cm. Texture: Smooth. Color: 137D.

*Reproductive organs.*—Stamens: Quantity: About 85 per flower. Anther size: Length, about 4 mm and width, about 1 mm. Anther shape: Ovate. Anther color: 13A. Pollen: Abundant, 10B in color. Pistils: Quantity: About 115 per flower. Pistil length: About 1.1 cm. Style color: 8C/180B. Stigma color: 5C. Ovary color: 155B.

Seed description:

*Length.*—About 7.5 mm.

*Width.*—About 4.5 mm.

*Color.*—159A.

Disease resistance: Moderate resistance to Powdery Mildew has been observed under commercial greenhouse production conditions.

It is claimed:

1. A new and distinct rose plant named 'Preveris', as illustrated and described.

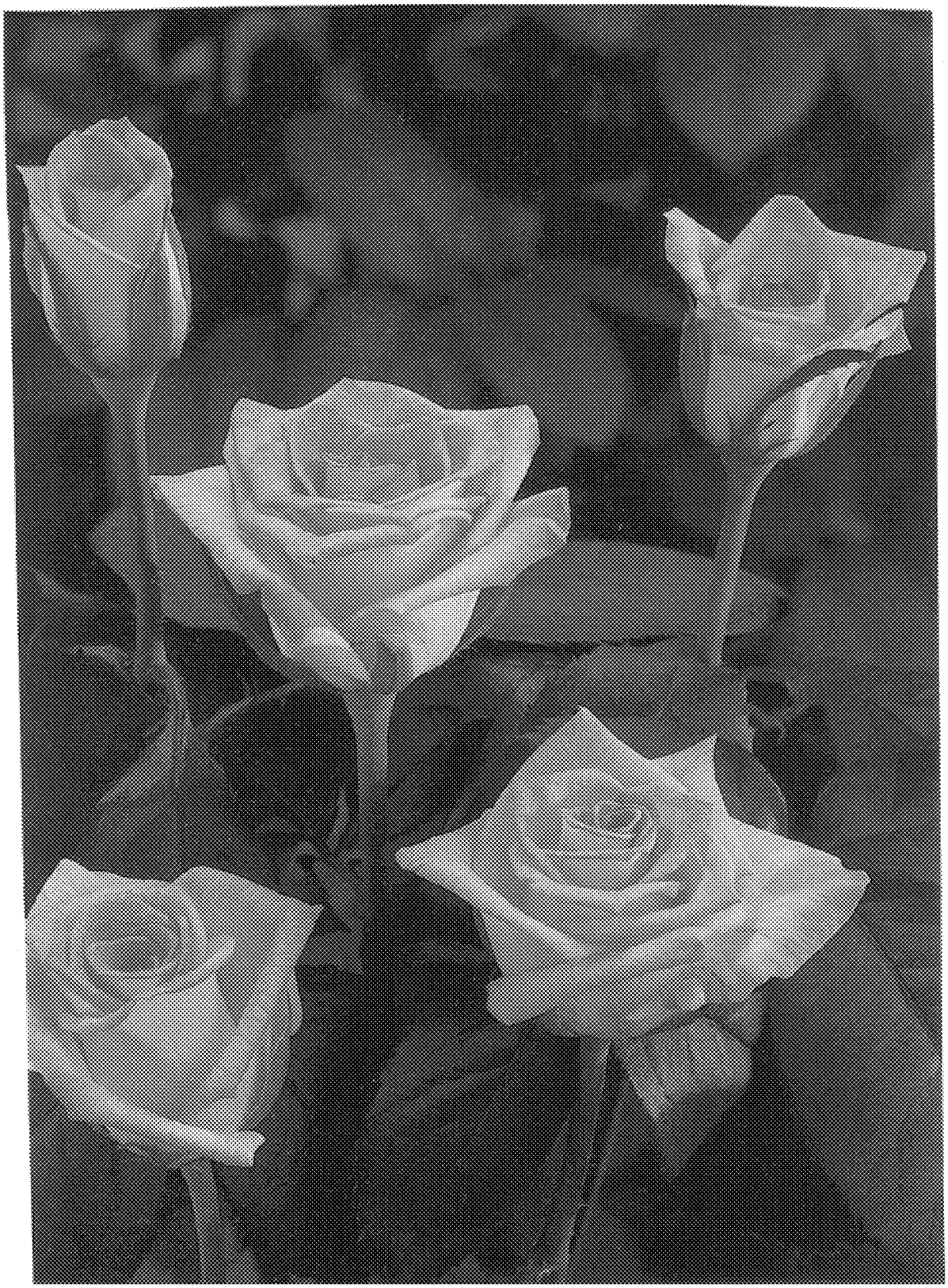

* * * * *